United States Patent
Chin et al.

(10) Patent No.: US 6,976,957 B1
(45) Date of Patent: Dec. 20, 2005

(54) CANNULA-BASED SURGICAL INSTRUMENT AND METHOD

(75) Inventors: Albert K. Chin, Palo Alto, CA (US); John P. Lunsford, San Carlos, CA (US); Tenny Chang, Mountain View, CA (US); Jeffrey W. Baxter, San Jose, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 0 days.

(21) Appl. No.: 10/773,770

(22) Filed: Feb. 6, 2004

Related U.S. Application Data

(63) Continuation of application No. 10/174,404, filed on Jun. 17, 2002, now abandoned, which is a continuation of application No. 09/634,132, filed on Aug. 8, 2000, now Pat. No. 6,406,425, which is a continuation of application No. 09/227,244, filed on Jan. 8, 1999, now Pat. No. 6,176,825, which is a continuation-in-part of application No. 09/102,723, filed on Jun. 22, 1998, now Pat. No. 5,895,353.

(51) Int. Cl.$^7$ ............................................. A61B 17/02
(52) U.S. Cl. ...................................... 600/205; 600/157
(58) Field of Search ................................ 600/155, 157, 600/205, 214

(56) References Cited

U.S. PATENT DOCUMENTS

| 4,557,255 | A | * | 12/1985 | Goodman | 600/104 |
|---|---|---|---|---|---|
| 5,843,121 | A | * | 12/1998 | Yoon | 606/206 |
| 5,857,961 | A | * | 1/1999 | Vanden Hoek et al. | 600/104 |
| 5,913,870 | A | | 6/1999 | DeFonzo et al. | |
| 5,957,936 | A | * | 9/1999 | Yoon et al. | 606/144 |
| 6,520,975 | B2 | * | 2/2003 | Branco | 606/159 |

* cited by examiner

*Primary Examiner*—Pedro Philogene
*Assistant Examiner*—David A Bonderer
(74) *Attorney, Agent, or Firm*—Fenwick & West LLP

(57) ABSTRACT

A retractor and a surgical tool are positioned within a cannula, and a dissection cradle of the retractor is positioned at the distal end of the cannula. The retractor includes a dissection cradle that is resiliently supported along an axis skewed relative to the axis of the cannula. The dissection cradle, in operation, is extended to cradle the target vessel, and the retractor may be fully extended to urge the vessel away from the axis of the cannula to isolate a side branch for exposure to a surgical tool. The retractor includes a hollow support and a spray nozzle disposed in the distal end of the retractor to form an irrigation system and lens washer that can be selectively positioned to direct the spray of irrigation fluid at a remote surgical site or at an endoscopic lens.

5 Claims, 13 Drawing Sheets

CANNULA-BASED SURGICAL INSTRUMENT AND METHOD

RELATED APPLICATIONS

This application is a continuation of application Ser. No. 10/174,404, filed on Jun. 17, 2002 now abandoned, which is a continuation of application Ser. No. 09/634,132, filed on Aug. 8, 2000 now U.S. Pat. No. 6,406,425 which is a continuation of application Ser. No. 09/227,244 filed on Jan. 8, 1999 now issued as U.S. Pat. No. 6,176,825, which is a continuation-in-part application of application Ser. No. 09/102,723 filed on Jun. 22, 1998, now issued as U.S. Pat. No. 5,895,353.

FIELD OF THE INVENTION

This invention relates to a cannula used for endoscopic surgery, and more particularly to a cannula and method for maintaining a clear visual field for an endoscope housed with the cannula.

BACKGROUND OF THE INVENTION

Endoscopic surgery allows a surgeon to perform safe and successful procedures because of the surgeon's ability to view the surgical site through the endoscope lens. For some surgical procedures, such as dissection, the cannula housing the endoscope has a transparent blunt dissection tip through which the surgeon views the surgical site. The blunt dissection tip protects the endoscope lens from being smeared by blood or fatty tissue present at the surgical site, or from being fogged due to the moist subcutaneous environment. However, many surgical procedures cannot be performed using a blunt dissection tip. When side branches and vessel ends of a vessel must be transected to harvest the vessel, the end of the cannula must be open to allow the surgical tools to extend from the cannula. When the cannula end is open, the endoscope lens is subject to the adverse conditions described above. The surgeon is forced to repeatedly remove the cannula from the body to clean the endoscope lens. This increases the length and risks of the operation.

Some conventional schemes for cleaning an endoscope lens rely upon an endoscope with a cleaning system built within it. However, having a cleaning system within the endoscope restricts the angle of incidence at which the cleaning fluid may be propelled toward the lens to almost parallel to the lens. This results in a less effective cleansing action. Also, since the spray is being directed parallel to the lens, the surgeon cannot see the spray source and it is therefore difficult to adjust the direction of the spray. Thus, with these systems, the endoscope must still be removed on occasion for manual cleaning where the proper angle of incident spray can be obtained manually. Additionally, in procedures using gas insufflation, the gas may dry out a target vessel or other surgical site. In these situations, it is often necessary to irrigate the vessel to prevent the vessel from drying out. However, conventional endoscope washing systems are not capable of providing both endoscope lens cleaning and remote surgical site irrigation. Therefore, a remote endoscopic washing system would be desirable for more effectively cleansing the endoscope lens during a surgical procedure by allowing the surgeon to control the angle at which cleansing fluid is sprayed as well as allowing the surgeon to use the same apparatus to irrigate the surgical site itself.

SUMMARY OF THE INVENTION

In accordance with the present invention, a retractor is positioned within a cannula with a dissection cradle end of the retractor positioned at the distal end of the cannula. The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having substantially parallel axes that selectively protrude from the distal end of the cannula. The protruding legs support the dissection cradle formed in the shape of a partial loop that is positioned in a plane skewed relative to the axes of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended, displacing the vein away from the axis of the cannula, causing the side branch to be isolated and exposed to a surgical tool. The surgical tool may then be extended from within the cannula to operate on the isolated and exposed side branch.

In accordance with one embodiment of the present invention, a remote irrigation system is built into the cannula. In one embodiment, one of the legs which comprise the retractor of the present invention is hollow, and is attached to a spray nozzle disposed in the distal end of the retractor. The proximal end of the hollow leg is attached to a fluid input tube which selectively provides irrigation fluid under pressure for washing the endoscope lens. When extended slightly beyond the distal end of the cannula, the spray nozzle is positioned to direct the spray of irrigation fluid at an angle approximately normal to the endoscope lens. This provides for an extremely effective cleaning action, and minimizes the need for removal of the endoscope during surgical procedures for manual cleaning. Additionally, if the surgical site itself requires irrigation, the retractor is extended out of the cannula toward the area requiring irrigation, and an irrigation fluid can be sprayed directly on the site. Finally, as the spray is directed back toward the lens, the surgeon can visually adjust the extension of the retractor to accurately direct the spray toward the lens or surgical site.

In a further embodiment, the hollow leg moves within a lumen in the cannula in fluid-resistant sliding engagement, and the fluid input tube is coupled to this lumen. In this embodiment, the maximal outer dimension of a region of the hollow leg is slightly less than a maximal inner dimension of the lumen. The slip-fit, fluid-resistant coupling of the hollow leg within the lumen allows irrigation fluid to be introduced at the proximal end of the lumen by the fluid input tube without significant leakage past the sliding juncture of the hollow leg within the lumen.

In an alternate embodiment, the hollow leg includes a semi-rigid plastic tubing, and fits within an irrigation tube which lines the inside of the lumen. The fluid input tube attaches to the irrigation tube and extends out of the cannula handle for receiving irrigation fluid. The use of flexible, semi-rigid plastic tubes provides fluid seals throughout the irrigation system to minimize leakage. In a third embodiment, the cannula contains a separate irrigation lumen which has a spray nozzle disposed in a fixed position at its distal end. The spray nozzle is positioned within the cannula to allow the proper angle of incidence for the spray to effectively clean the lens. Finally, in another embodiment, the dissection cradle is supported by only one leg, and the lumen which previously held the second leg instead is fitted with a spray nozzle directed toward the endoscope lens. An embodiment is also disclosed in which a nozzle tube situated within a cannula lumen is selectively extensible responsive to the application of hydraulic pressure.

BRIEF DESCRIPTION OF THE DRAWINGS

FIG. 7b is a side view of the retractor 112 of FIG. 7a.

FIG. 10b illustrates a side view of the cradle 116 of FIG. 10a.

FIG. 11d is an alternate embodiment of the cannula-based irrigation system of FIG. 11a.

DETAILED DESCRIPTION OF THE PREFERRED EMBODIMENTS

Figure 1:
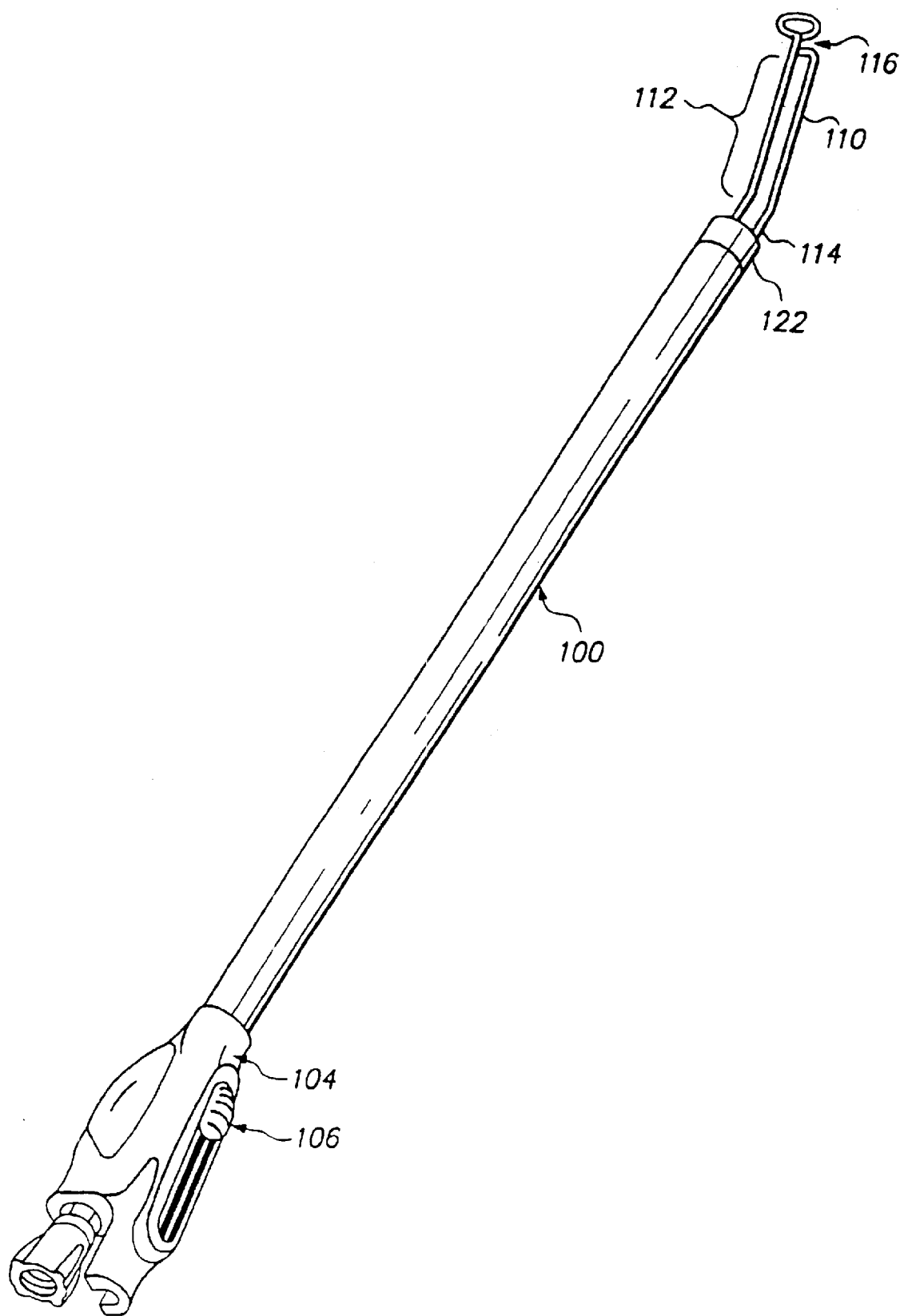
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bioinert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
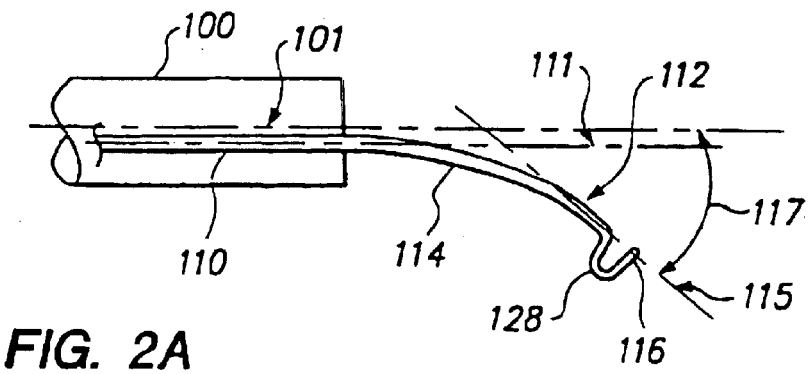
FIG. 2a is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula. The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and resilient plastic. In one embodiment, the retractor 112 includes a coating for lubrication, insulation, and low visual glare using, for example, parylene or nylon 11.

Figure 2B:
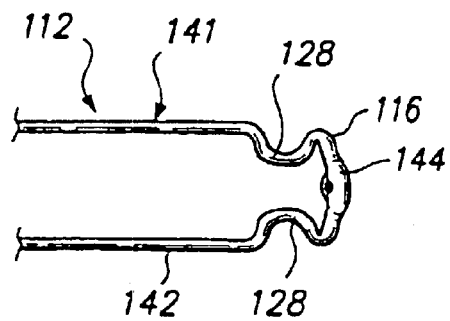
FIG. 2b is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest.

The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
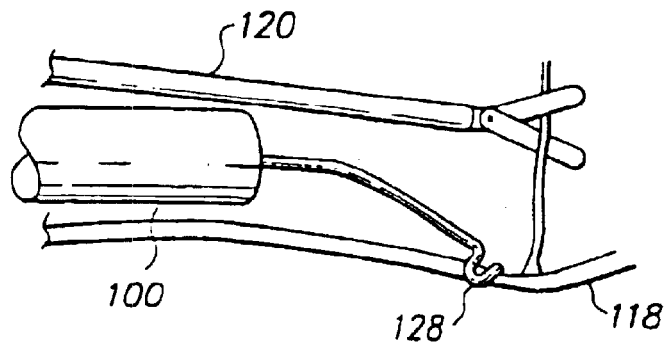
FIG. 3a is a perspective side view of cannula 100 with a saphenous vein positioned within the cradle 116.

FIG. 3a illustrates a perspective view of the cannula 100 in accordance with the present invention with the retractor fully extended, holding a saphenouss vein 118, and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein, vessel, tissue or organ of interest, and surgical tool 120 may be any surgical tool suitable for performing a surgical procedure near the dissection cradle 116.

Figure 3B:
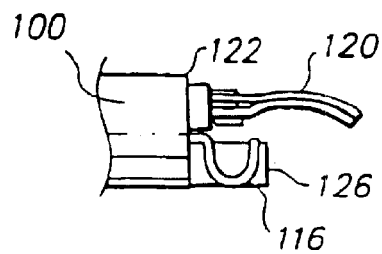
FIG. 3b is a perspective side view of the distal end 122 of cannula 100 in an embodiment in which an endoscope 126 and a surgical tool 120 are present and partially extended.
Figure 3C:
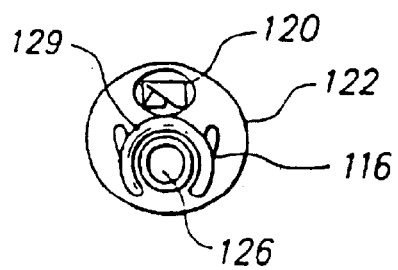
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as cauterizing scissors, used to sever a tributary or side branch of a saphenouss vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
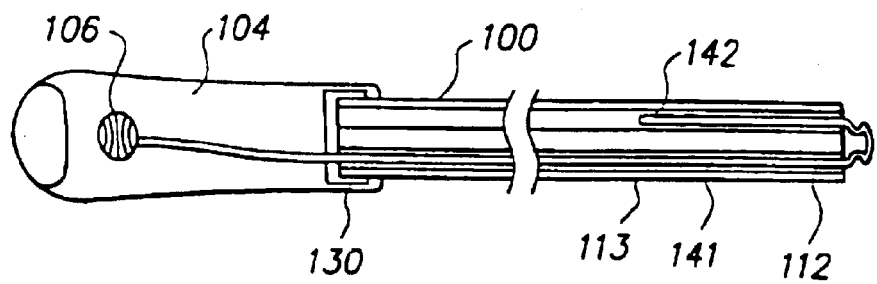
FIG. 4a is a cut-away top view of cannula 100.
Figure 4B:
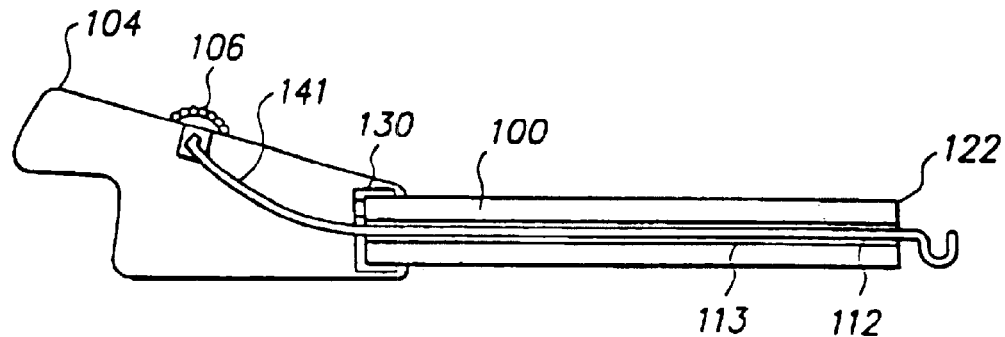
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 112 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 translationally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a, and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula. The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the saphenouss vein 118. When retracted into the cannula 100, the retractor 112 is again resiliently straightened or flattened.

Figure 5A:
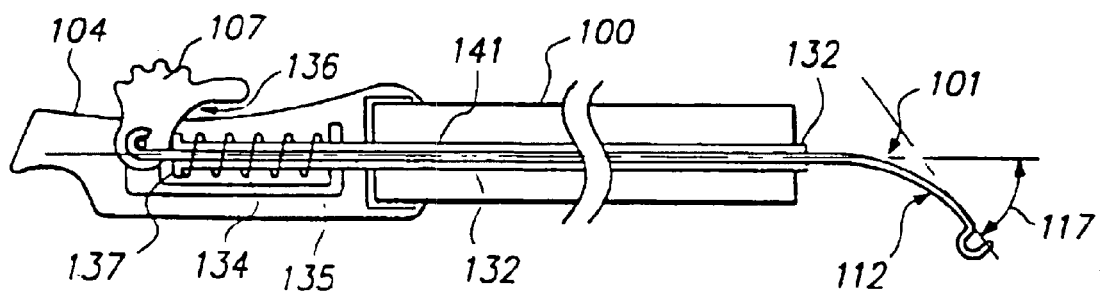
FIG. 5a is a cut-away view of a sliding tube embodiment of cannula 100 in a first position.
Figure 5B:
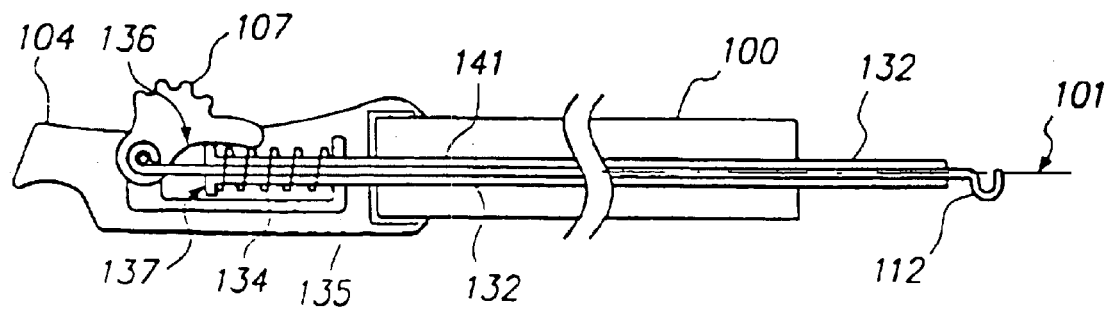
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 132, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG. 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward, overcoming the resilient force of spring 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
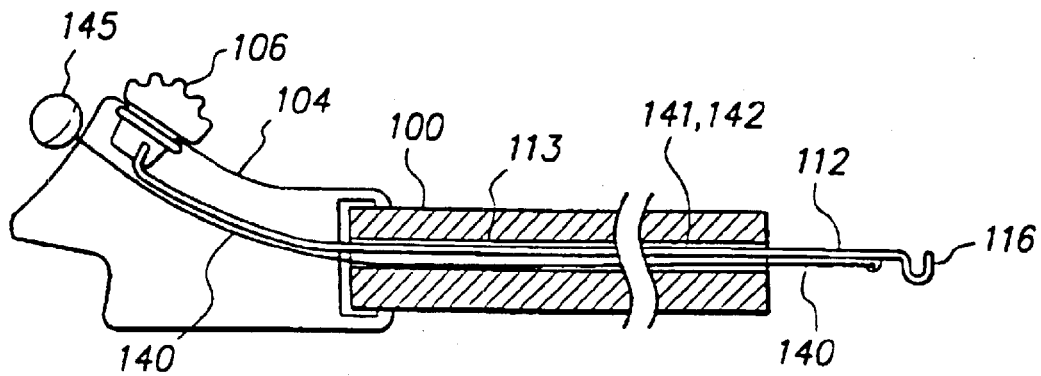
FIG. 6a is a cut-away view of an embodiment of cannula 100 having an angling device 140.
Figure 6B:
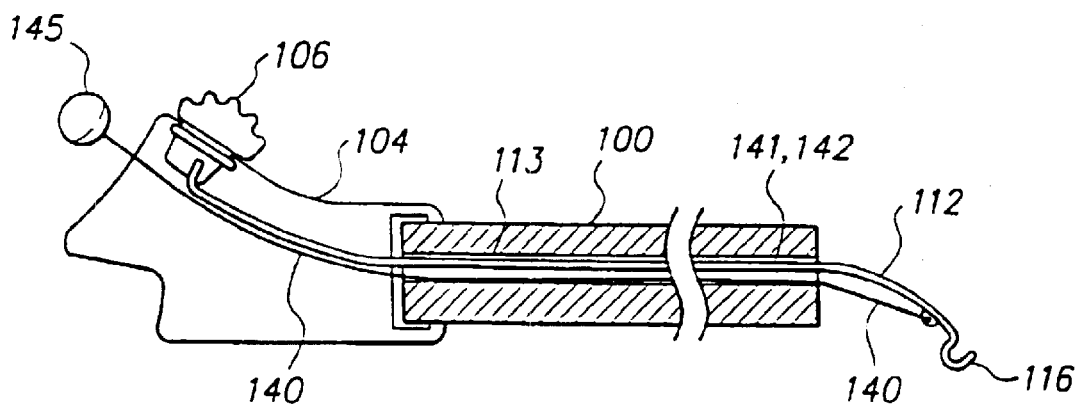
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
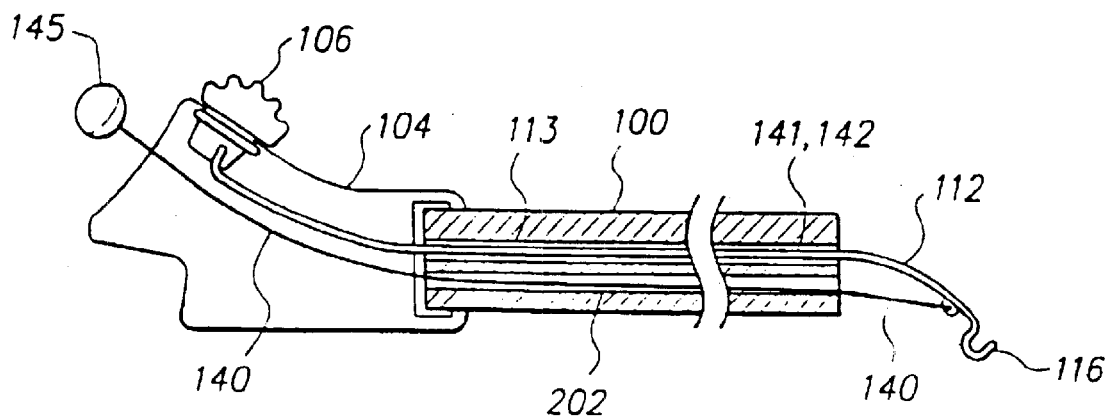
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended, the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
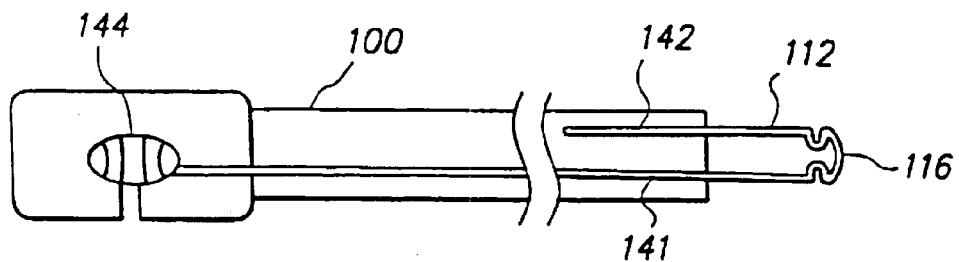
FIG. 7a is a cut-away side view of a twistable retractor 112 in a straight position.
Figure 7C:
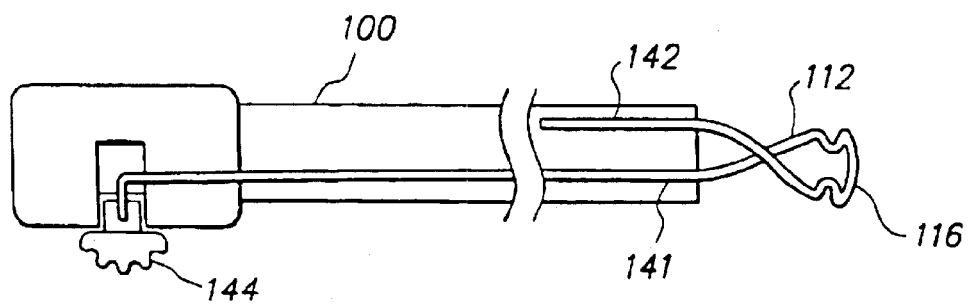
FIG. 7c is a cut-away side view of twistable retractor 112 in a crossed position.
Figure 7B:
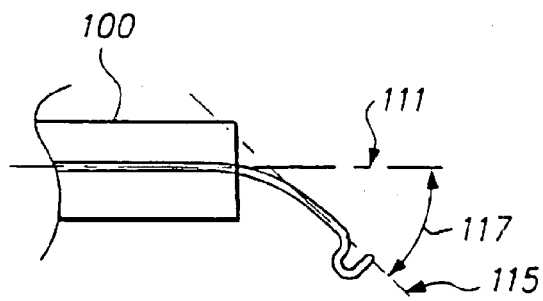
Figure 7D:
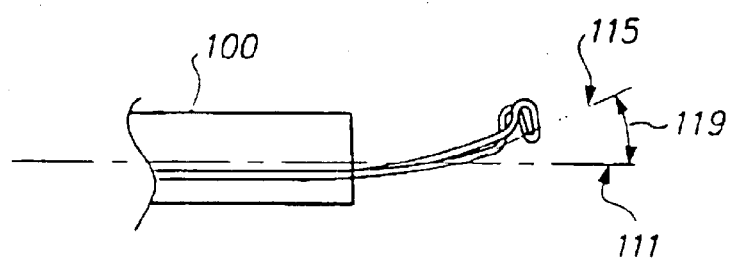
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 147 for convenient manual manipulation of this embodiment of the invention. Upon sliding the knob 147, the leg 142 coupled to knob 147 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 147 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 112 is in the first position, then upon rotating the knob 147, the vessel is transported to the other side of the cannula 100. This allows the user to isolate the vessel by simply actuating knob 147.

Figure 8A:
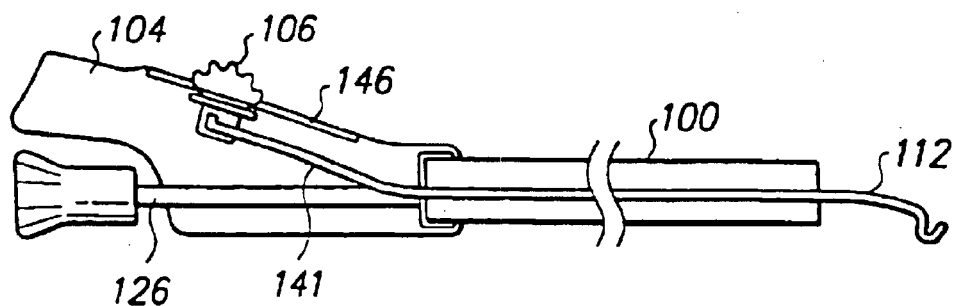
FIG. 8a is a cut-away side view of the handle 104.
Figure 8B:
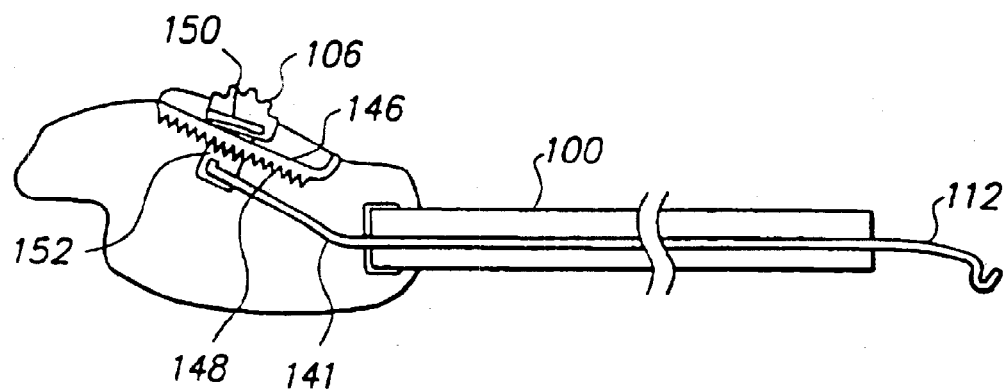
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction of the leg 141, button 106 is released and is retained place by the engaged teeth 148, 152.

Figure 9A:
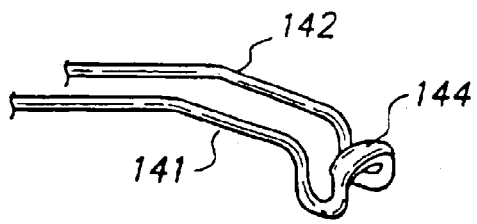
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support for the target vessel retained within cradle 116. Additionally, by minimizing the thickness of distal portion 144, contact with other devices in close proximity with retractor 112 is minimized.

Figure 9B:
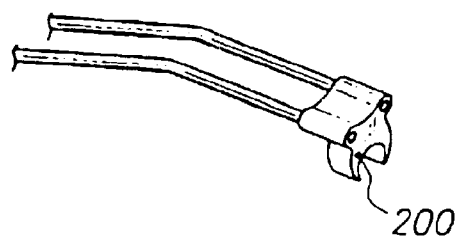
FIG. 9b illustrates a first alternate embodiment of cradle 116.
Figure 10A:
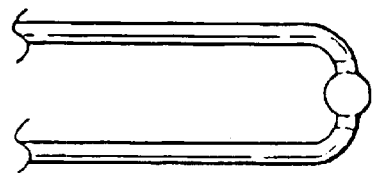
FIG. 10a illustrates a top view of an embodiment of the cradle 116 of FIG. 9c without a "C" ring.
Figure 10B:
Figure 10C:
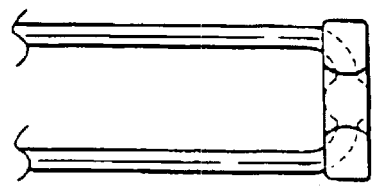
FIG. 10c illustrates a top view of the cradle 116 of FIG. 9c with the "C" ring attached.
Figure 10D:
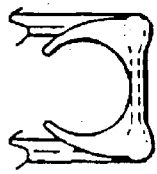
FIG. 10d illustrates a side view of the cradle 116 of FIG. 10c.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIG. 10c and 10d.

Figure 9C:
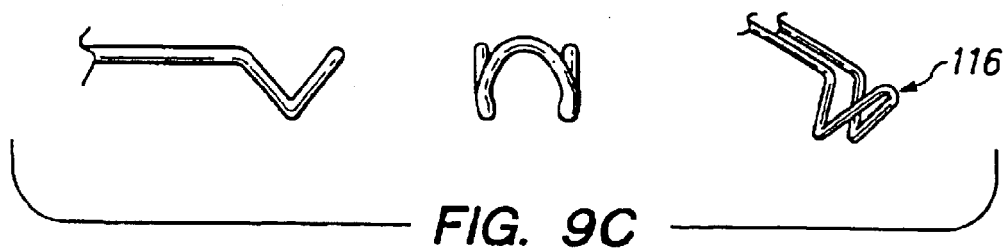
FIG. 9c illustrates multiple views of a second alternate embodiment of cradle 116.
Figure 9D:
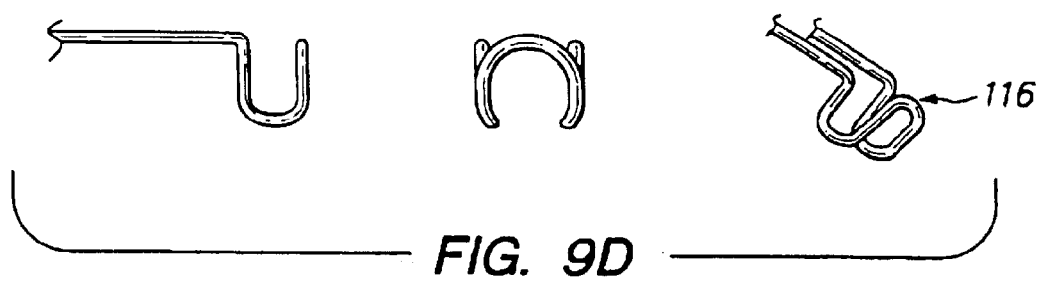
FIG. 9d illustrates multiple views of a third alternate embodiment of cradle 116.
Figure 9E:
FIG. 9e illustrates multiple views of a fourth alternate embodiment of cradle 116.
Figure 9F:
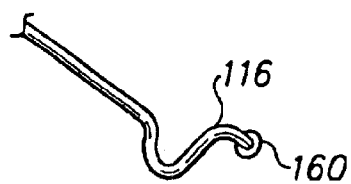
FIG. 9f illustrates multiple views of a fifth alternate embodiment of cradle 116.
Figure 9G:
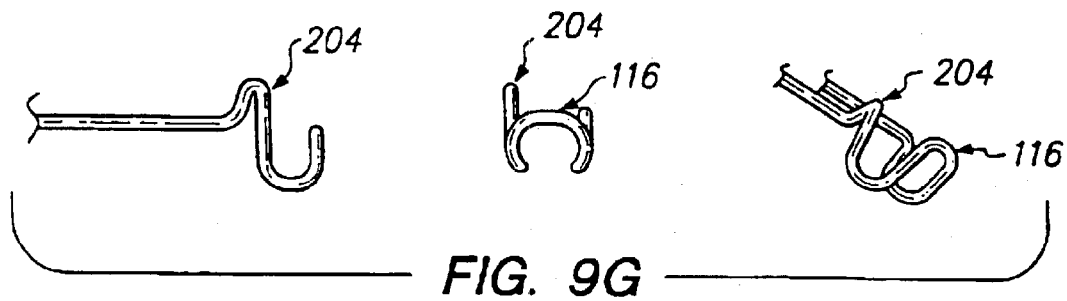
FIG. 9g illustrates multiple views of an embodiment of cradle 116 having a spur.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

Figure 11A:
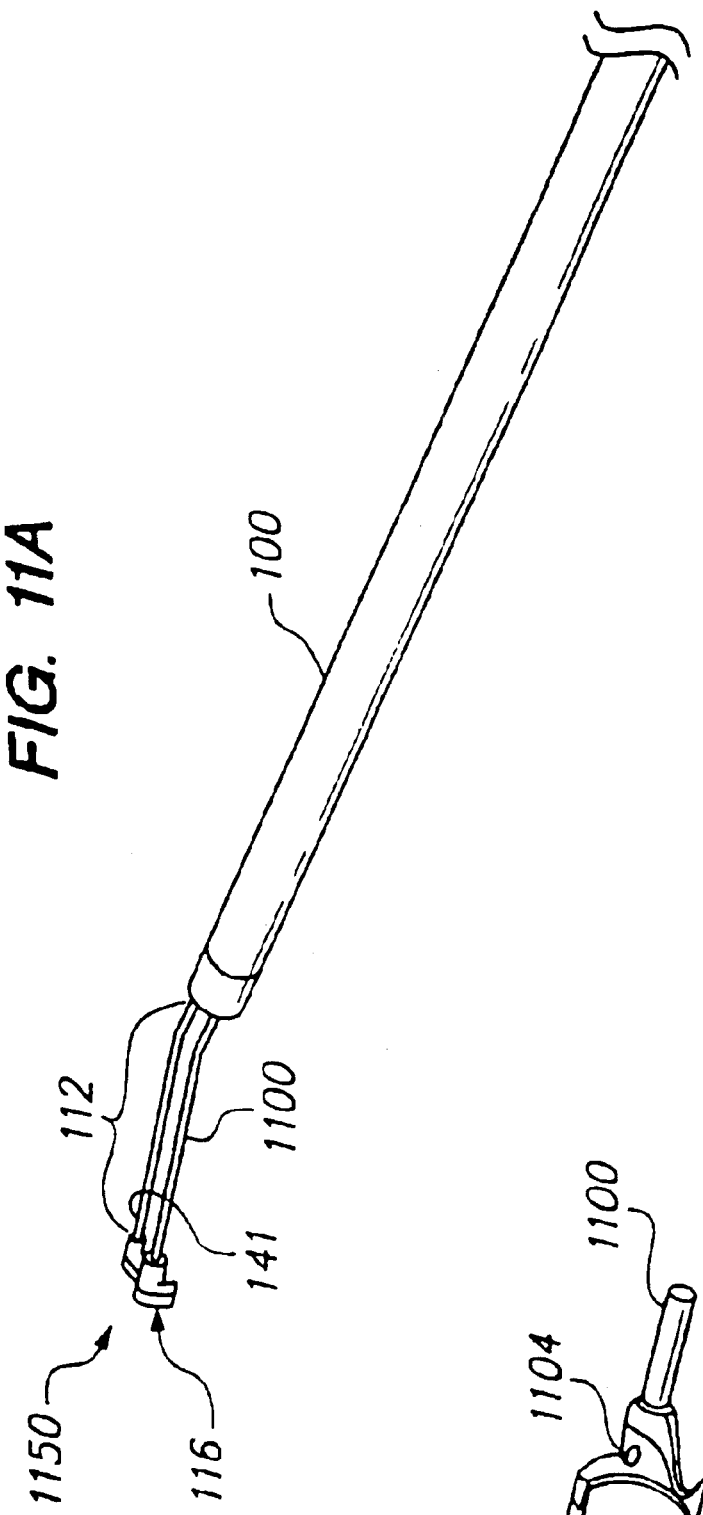
FIG. 11a illustrates a perspective side view of a cannula 100 including an irrigation system integrated with the retractor 112.
Figure 11B:
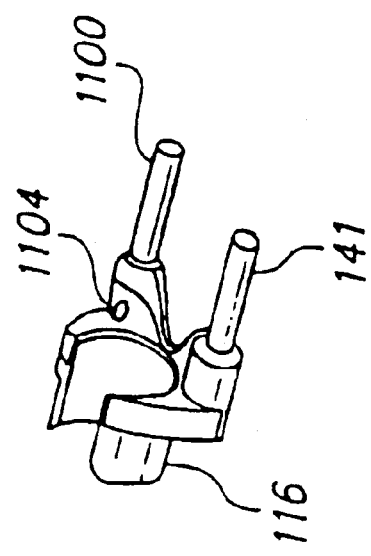
FIG. 11b is a cut-away view of a retractor 112 of FIG. 11a modified to incorporate the irrigation system.

FIG. 11a illustrates a perspective side view of a cannula 100 and an irrigation effector 1150 for cleaning an endoscope lens 1108 and wetting a surgical site. In the embodiment of FIG. 11a, the irrigation effector is retractor 112. As described above, the retractor 112 extends distal to the tip of the cannula 100 responsive to activation of a control button 106. In one embodiment, two supporting members 1100, 141 attach to the dissection cradle 116 and allow it to extend and retract. As shown in FIG. 11b, one supporter or leg 1100 is hollow, functioning as a lumen to carry irrigation fluid for cleaning an endoscope lens 1108 (shown in FIG. 11c). An irrigation nozzle 1104 is disposed on the cradle 116 or on the distal portion of the hollow leg 1100 and is configured to spray irrigation fluid at the endoscopic lens 1108. The irrigation fluid is received from a fluid source which conducts the fluid under pressure to the leg 1100. When the retractor 116 is slightly extended out of the distal end of the cannula 100, the irrigation nozzle 1104 is directed toward the lens 1108 of the endoscope 126 at an angle approximately normal to the endoscope lens 1108, allowing a spray of irrigation fluid to contact the surface of the lens 1108 and clean the lens 1108 effectively. Additionally, as the spray is directed back toward the endoscope 126, the surgeon is able to view the source of the spray through the endoscope 126, and is able to adjust the angle of incidence by adjusting the extension of the retractor 112. Thus, by having the endoscopic washing system built into the cannula 100 and into the sliding retractor 112, a more effective cleaning system is provided than what is provided by systems which are built into the endoscope itself.

If the surgical site requires irrigation, the dissection cradle 116 is extended out of the cannula 100, as shown in FIG. 11a, toward the area requiring irrigation. Upon reaching the site under endoscopic visualization, the surgeon can direct a spray of irrigation fluid toward the site. Again, if the site is not properly irrigated, the surgeon can adjust the positioning of the retractor 112 until the spray has contacted the surgical site. Thus, the irrigation system of the present invention can both wash the endoscope lens 1108 and irrigate a remote surgical site.

Figure 11C:
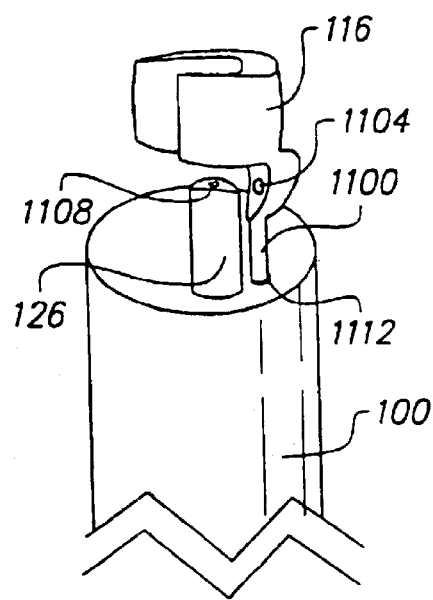
FIG. 11c is a cut-away view of a modified retractor 112 and endoscope 126 situated in a cannula 100.
Figure 11D:
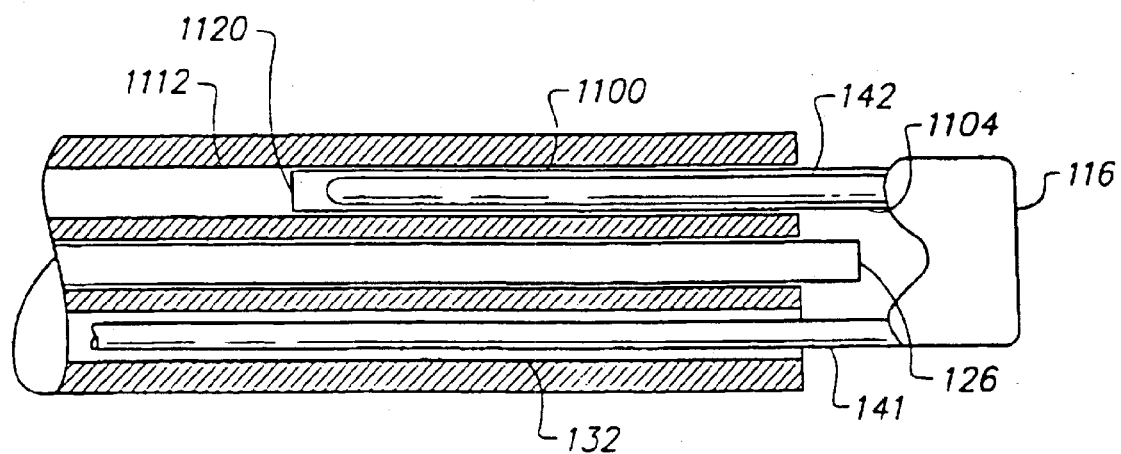

As shown in FIG. 11c, the hollow leg 1100 is situated within a lumen 1112 in the cannula body 100. An extension tube (not shown) is connected to the proximal end of the lumen 1112 to provide a source of irrigation fluid under pressure, for example, via a Luer lock syringe fitting. The syringe is used to selectively inject fluid under pressure into the lumen 1112 upon a determination that the endoscope lens 1108 requires cleansing. The hollow leg 1100 may extend only a fraction of the length of the lumen 1112 within the cannula body 100 prior to coupling to irrigation fluid under pressure. However, the hollow leg 1100 should be of sufficient length to extend the cradle 116 out to its proper working distance. To minimize leakage of irrigation fluid, the hollow leg 1100 has an outer diameter that slip fits within the inner diameter of the cannula body lumen 1112. Alternatively, as shown in FIG. 11d, the hollow leg 1104 has an outer diameter smaller than the inner diameter of the cannula body lumen 1112, but has a proximal end 1120 that flares out to a slip fit within the cannula body lumen 1112. These relative dimensions allow irrigation fluid to be dispensed through the cannula body lumen 1112, into the hollow leg 1100 and out the irrigation nozzle 1104 without significant leakage past the hollow leg 1100.

FIG. 11d illustrates an embodiment of the single-leg irrigation system in which a wire 141 is present within the hollow leg 1100 in lumen 113. The presence of wire 141 provides support and rigidity to the retractor 112 while retaining the ability of the hollow leg 1100 to be used to conduct irrigation fluid to the irrigation nozzle 1104.

Figure 12:
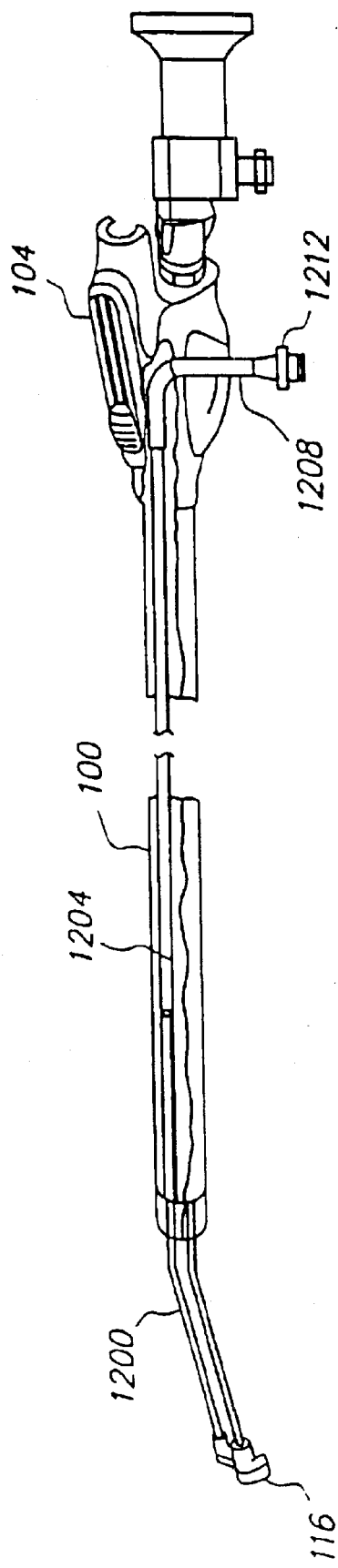
FIG. 12 is a cut-away side view of a multi-tube embodiment of an irrigation system.

FIG. 12 is a cut-away side view of a multi-tube embodiment of a cannula-based irrigation system. In this embodiment, the hollow leg 1200 includes a semi-rigid flexible tube or the like, and extends approximately one quarter to one third of the length of the cannula body 100 within a second irrigation tube 1204 inside of the cannula body lumen 1112. A fluid input tube 1208 of flexible plastic attaches to the proximal end of the irrigation tube 1204 and extends out of the cannula handle 104. The proximal end of the fluid input tube 1208 may include a valved Luer lock fitting 1212 for connection to a source of irrigation fluid such as provided by a syringe by selective applications of pressure. The first tube 1200 is slidable within the irrigation tube 1204 to form an adequate sliding fluid seal between the moving parts.

Figure 13:
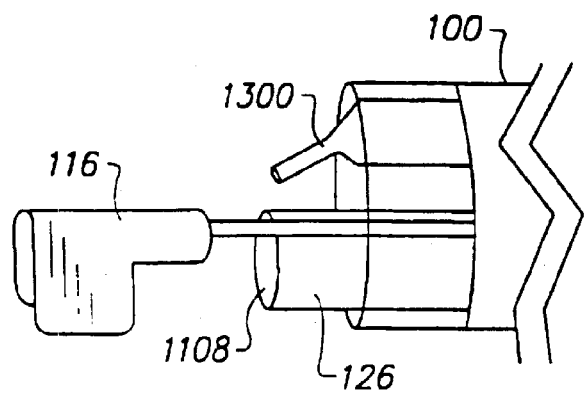
FIG. 13 is a cut-away side view of an irrigation system including a separate lumen.

FIG. 13 is a cut-away side view of a separate lumen irrigation system. In this embodiment, the cannula 100 contains a separate irrigation lumen in the cannula body. The lumen ends in a spray nozzle 1300 on the distal tip of the cannula 100. The tip of the nozzle 1300 is approximately parallel to the lens 1108. Cleansing is accomplished by applying spraying irrigation fluid across the lens 1108 to wash the lens 1108. The irrigation fluid is supplied to the irrigation lumen by a fluid input tube 1208 as described above in FIG. 12, and the proximal end of the fluid tube 1208 may be attached to a syringe as a source of the irrigation fluid under selective pressurization. The syringe may be removeably attached to the cannula handle 104 to prevent the syringe from moving or dangling from the handle 104, and obtruding on manipulation of the cannula 100 during vessel harvesting.

Figure 14A:
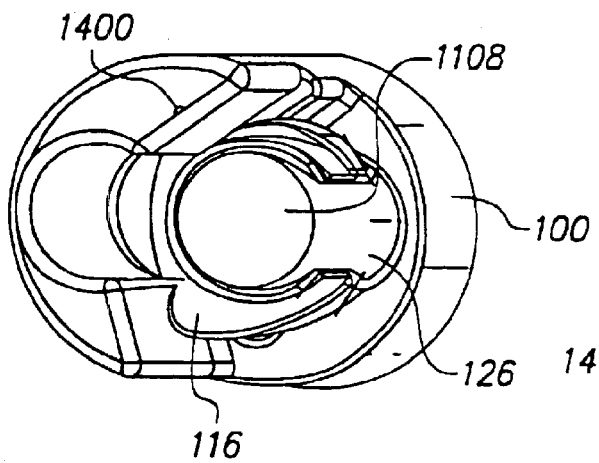
FIG. 14a is a perspective front view of a single leg irrigation system.
Figure 14B:
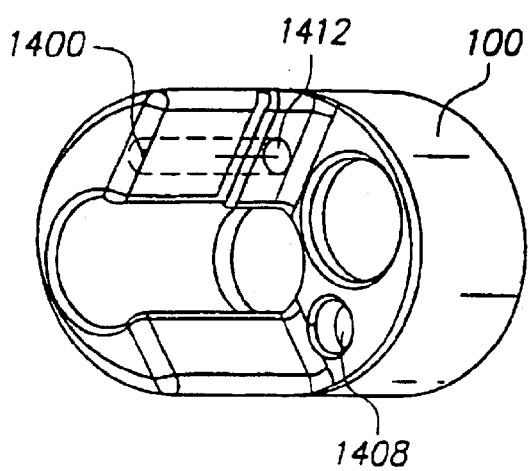
FIG. 14b is a perspective side view of the single leg irrigation system.

FIG. 14a is a perspective front view of a single leg irrigation system and shows the distal end of the cannula 100 housing the cradle 116 and the endoscope 126. In this embodiment, the dissection cradle 116 is supported by one leg 141 (shown in FIG. 11b) within a first lumen 1408 within the cannula body 100, and a cannula body lumen 1412 not occupied by the second leg of the cradle 116, as in embodiments previously described, is fitted with a nozzle 1400 which sprays the endoscope lens 1108. The spray nozzle 1400 is directed at an angle at which the endoscope lens 1108 can be sprayed directly and effectively for cleaning. FIG. 14b is a perspective side view of the single leg irrigation system and shows the distal end of the cannula 100 and the location of the spray nozzle 1400.

Figure 15:
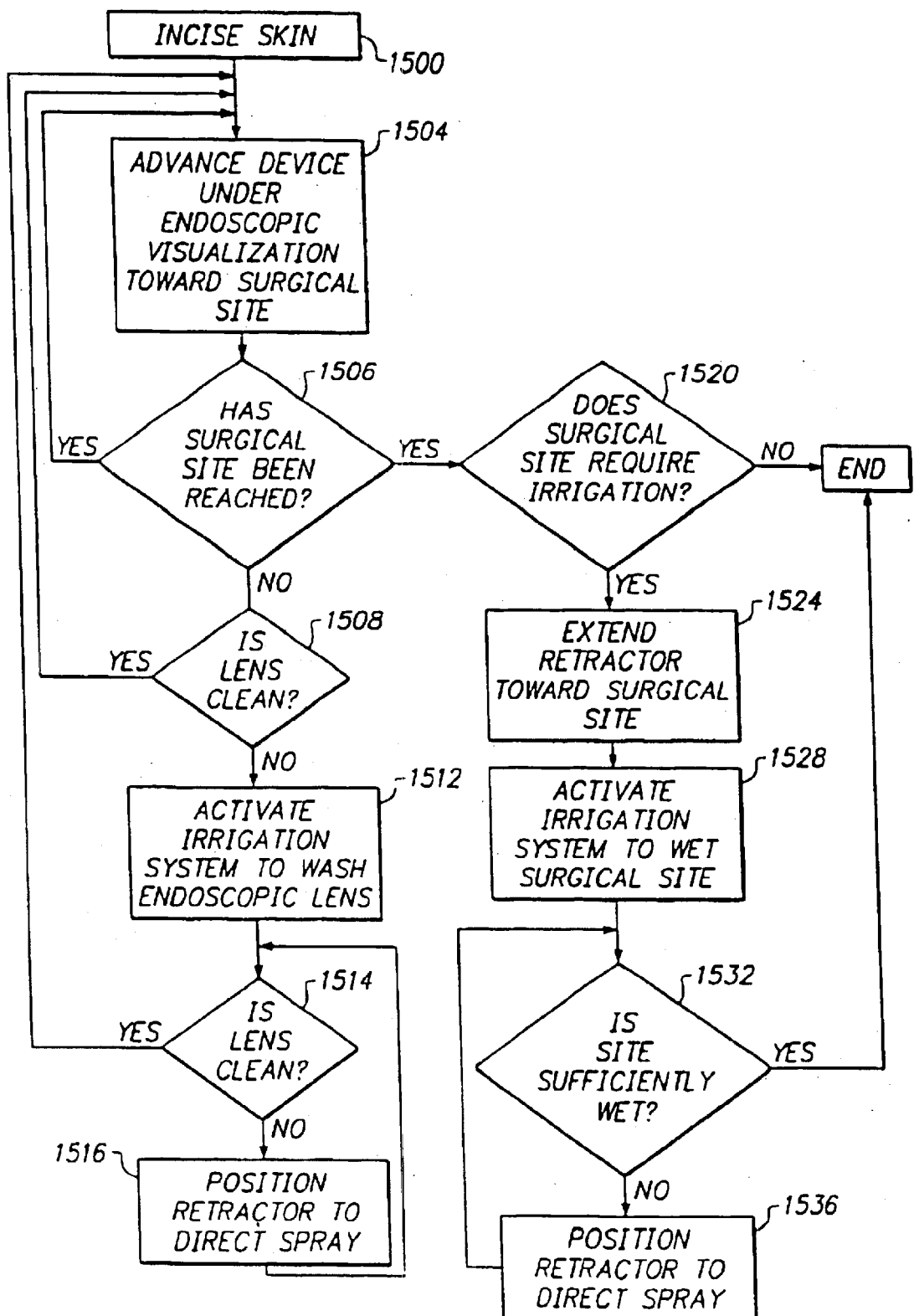
FIG. 15 is a flowchart illustrating a method of cleansing an endoscopic lens and irrigating a surgical site in accordance with the present invention.

FIG. 15 is a flowchart illustrating a method for washing an endoscopic lens 1108 and remote surgical site in accordance with the present invention. First, skin is incised 1500 at an area near a target vessel. Next, the device is advanced 1504 under endoscopic visualization toward the surgical site. If the surgeon determines 1506 that the surgical site has been reached, then the surgeon determines 1520 whether the surgical site requires irrigation. If the surgical site requires irrigation, the surgeon extends 1524 the retractor 112 toward the surgical site and activates 1528 the irrigation system to wet the surgical site. The surgeon determines 1532 whether the site is sufficiently wet by viewing the site through the endoscope 126. If the site is sufficiently wet, the process ends. If the site requires more irrigation, the surgeon positions 1536 the retractor 112 under endoscopic visualization to direct the spray more accurately at the surgical site.

If the surgical site has not been reached, the surgeon determines 1508 whether the lens 1108 is clean. In response to the lens 1108 becoming obscured with blood, fatty tissue, or the like, the irrigation system is activated 1512 in situ to wash the lens 1108. In one embodiment as described above, the retractor 112 is extended until the angle of the spray is approximately normal to the surface of the endoscopic lens 1108, and therefore effectively washes the lens 1108. Next, the surgeon determines 1514 whether the lens 1108 has been cleaned satisfactorily. If not, the retractor and thereby the irrigation nozzle 1104 is selectively positioned 1516 via extension or retraction of the retractor 112 under endoscopic visualization to direct the spray toward the lens 1108 at a more effective angle. The surgeon can continue to reposition the retractor 112 until the spray nozzle is directed at an effective angle toward the lens 1108.

Figure 16A:
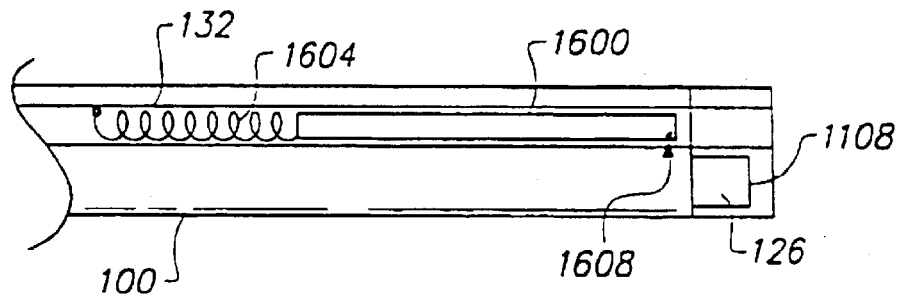
FIG. 16a is a cut-away side view of an alternate embodiment of a cannula-based irrigation system in accordance with the present invention.
Figure 16B:
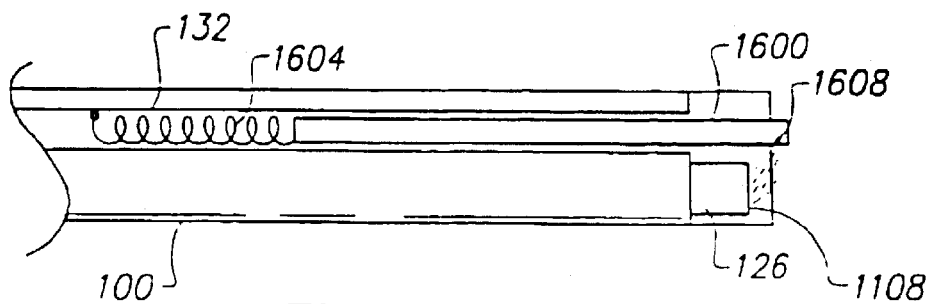
FIG. 16b illustrates the embodiment of FIG. 16a when the nozzle 1600 is under hydraulic pressure.

FIG. 16a shows a cut-away side view of another embodiment of a cannula-based irrigation system. In this embodiment, a nozzle tube 1600 is extendable from within a lumen 113 in the cannula 100. The proximal end of the nozzle tube 1600 is attached to a distal end of a tension spring 1604, whose proximal end is stably attached on the side of the lumen 113 or at the proximal end of the cannula 100. The tension spring 1604 biases the nozzle tube 1600 in a retracted state. Upon exposure to hydraulic water pressure, as shown in FIG. 16b, the liquid pushes the nozzle tube 1600 out of the lumen to a point slightly beyond the endoscope lens 1108. The liquid flows inside the nozzle tube 1600 and exits out the spray hole 1608, spraying irrigation fluid back towards the endoscope lens 1108.

Thus, the irrigation systems described above provide an effective method of cleaning an endoscope lens 1108 without requiring the removal of the endoscope from a surgical site. Additionally, the washing system described above is more effective due to the use of a spray nozzle external to the endoscope, which allows the angle of spray to be directly projected against the endoscope lens 1108. In an embodiment in which the irrigation nozzle 1104 is disposed on the cradle 116 or on the hollow leg 1100, a surgeon can visually adjust the angle of incidence of the spray, and can also irrigate a surgical site by adjusting the extension of the retractor 112 out of the cannula 100.

What is claimed is:

1. Surgical apparatus comprising:

an elongated cannula having an elongated axis between distal and proximal ends, and including an endoscope lumen extending as a hollow bore between the distal and proximal ends for slidably receiving an endoscope therein;

an instrument lumen extending as a hollow bore between distal and proximal ends of the cannula in substantial diametric orientation therein relative to the endoscope lumen;

an auxiliary lumen extending as a hollow bore between distal and proximal ends of the cannula in substantially orthogonal orientation therein relative to the diametric orientation of the endoscope lumen and instrument lumen; and an elongated support slidably disposed within the bore of the auxiliary lumen to selectively extend beyond the distal end of the cannula, and including an end effector mounted distally on the elongated support for movement therewith beyond the distal end of the cannula.

2. Surgical apparatus comprising:

an elongated cannula having an elongated axis between distal and proximal ends, and including an endoscope lumen extending as a hollow bore between the distal and proximal ends for slidably receiving an endoscope therein;

an instrument lumen extending as a hollow bore between distal and proximal ends of the cannula in the substantial diametric orientation therein relative to the endoscope lumen;

a pair of auxiliary lumens extending as hollow bores between distal and proximal ends of the cannula in substantially diametric orientation on opposite sides of, and in skewed relation to, the diametric orientation of the endoscope lumen and instrument lumen; and elongated supports slidably disposed within the bores of the pair of auxiliary lumens to selectively extend beyond the distal end of the cannula, and including a vessel cradle mounted to traverse the distal ends of the elongated supports.

3. Surgical apparatus according to claim 2 in which the vessel cradle includes a substantially U-shaped transverse segment between the elongated supports for positioning about the distal end of an endoscope received in the endoscope lumen.

4. Surgical apparatus according to claim 2 including a manual control element attached to an elongated support and disposed for manually activated sliding movement thereof near the proximal end of the cannula.

5. Surgical apparatus according to claim 4 including a resilient elongated support attached to the manual control element for sliding movement thereof near the proximal end of the cannula along a direction skewed relative to the elongated axis of the cannula.

* * * * *